(12) United States Patent
Shin et al.

(10) Patent No.: US 7,642,356 B2
(45) Date of Patent: Jan. 5, 2010

(54) PROCESS FOR PREPARING BETA-KETOESTER COMPOUNDS

(75) Inventors: Hyun Ik Shin, Daejeon (KR); Bo Seung Choi, Daejeon (KR); Jae Hoon Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 12/065,752

(22) PCT Filed: Sep. 15, 2006

(86) PCT No.: PCT/KR2006/003683

§ 371 (c)(1),
(2), (4) Date: Mar. 5, 2008

(87) PCT Pub. No.: WO2007/064077

PCT Pub. Date: Jun. 7, 2007

(65) Prior Publication Data

US 2008/0221333 A1      Sep. 11, 2008

(30) Foreign Application Priority Data

Sep. 16, 2005   (KR)   ................. 10-2005-0086992

(51) Int. Cl.
*C07D 211/72* (2006.01)
*C07C 381/00* (2006.01)
*C07C 205/00* (2006.01)

(52) U.S. Cl. ............................ 546/312; 540/20; 540/78
(58) Field of Classification Search .................. 546/289, 546/286, 304, 310, 183; 560/78, 20
See application file for complete search history.

(56) References Cited

U.S. PATENT DOCUMENTS 6,500,797 B1    12/2002   Ortiz et al.

FOREIGN PATENT DOCUMENTS

| JP | 58-144381 A | 8/1983 |
|----|----|----|
| JP | 4-270244 A | 9/1992 |
| WO | WO-03/033469 A1 | 4/2003 |

OTHER PUBLICATIONS

"Efficient and Scalable Synthesis of Ethyl 2,6-Dichloro-5-Fluornicotinoyl Acetate Using the Blaise Reaction as a Key Step", Choi et. al., Organic Process Research & Development, vol. 9, No. 3, 2005.*

* cited by examiner

*Primary Examiner*—Janet L Andres
*Assistant Examiner*—Binta M Robinson
(74) *Attorney, Agent, or Firm*—Birch, Stewart, Kolasch & Birch, LLP

(57) ABSTRACT

The present invention relates to a process for preparing a beta-keto ester compound of formula (1), which is an intermediate for the synthesis of quinolone antibiotics. Particularly, the present invention is characterized by the reaction of an organo nitrile compound with a salt of mono-alkyl malonate in the presence of metal salt, and so the reaction is easy to control due to its endothermic nature, and is devoid of lachrymatory reagents with excellent reproducibility. Subsequent in situ hydrolysis in the presence of aqueous acid solution provided the compound of formula (1).

17 Claims, No Drawings

PROCESS FOR PREPARING BETA-KETOESTER COMPOUNDS

TECHNICAL FIELD

The present invention relates to a process for preparing a beta-keto ester compound of the following formula (1) by reacting an organo nitrile compound with a salt of mono-alkyl malonate in the presence of metal salt, followed by acid hydrolysis;

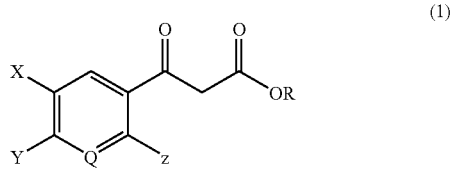

wherein Q represents C—H, C—$NO_2$, C—F, C—OMe or N; X, Y and Z each independently represent H, halogen or $NO_2$; and R represents straight or branched $C_1$-$C_6$-alkyl or benzyl.

BACKGROUND ART

The beta-keto ester compound of formula (1) is an important intermediate for the synthesis of various quinolone antibiotics (e.g. ciprofloxacin, levofloxacin, trovafloxacin, gemifloxacin, etc.) which show potent antibiotic activities, and so has been used as an agent for the treatment of bacterial infection of human or animal.

The beta-keto ester compound of formula (1) is generally synthesized through a three-step process (see: Synthesis, 1993, 290; Org. Prep. Proc. Int., 1997, 29, 231).

The three-step synthesis process is recently reduced to one-step process by using the Blaise reaction, in which a new zinc activation method by a catalytic amount of organic acid was established with good reproducibility (see: WO 03033469; Synthesis, 2004, 16, 2629), as shown in the following Reaction Scheme 1.

Reaction Scheme 1

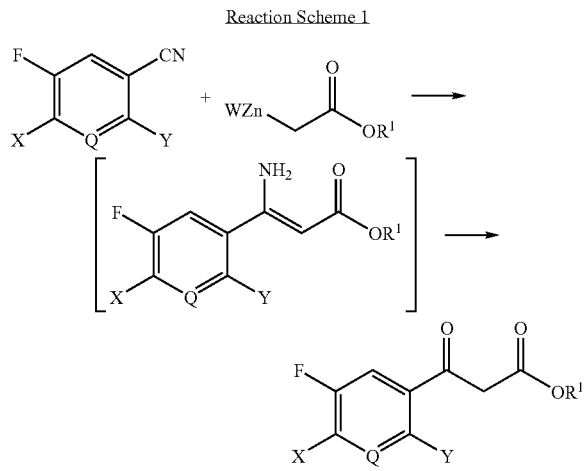

However, despite the above merits, the process using the Blaise reaction still has the following problems: (1) it is highly exothermic, and so is difficult to control the reaction heat, (2) it is difficult to handle alkyl alpha bromo acetate due to the lachrymal property, and (3) an excess amount of zinc metal having high density makes the stirring difficult, and is occasionally deposited at the bottom of the reactor, thereby lowering the reaction reproducibility.

DISCLOSURE OF THE INVENTION

To improve the above problems, the object of the present invention is to provide a process for preparing various beta-keto ester compounds from organo nitrile compounds by using a reactant that does not generate uncontrollable exotherm, and is devoid of lachrymatory reagent with excellent reproducibility.

DETAILED DESCRIPTION OF THE INVENTION

The present invention provides a process for preparing beta-keto ester compound of the following formula (1),

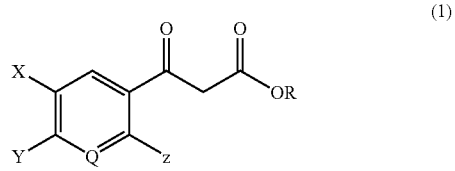

wherein,
Q represents C—H, C—$NO_2$, C—F, C—OMe or N,
X, Y and Z each independently represent H, halogen or $NO_2$, and
R represents straight or branched $C_1$-$C_6$-alkyl or benzyl,
comprising the steps of,
1) reacting the compound of the following formula (2) with the compound of the following formula (3) in the presence of metal salt,

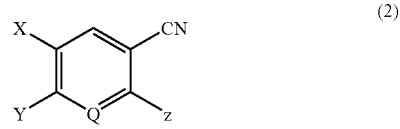

wherein Q, X, Y and Z are defined as above, and

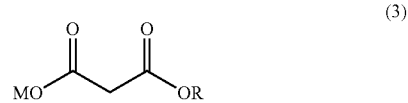

wherein R is defined as above and M represents alkali metal; and,
2) hydrolyzing the compound obtained from the step 1) in the presence of aqueous acid solution.

Hereinafter, the present invention is specifically illustrated on the basis of the reaction schemes below. However, the reaction schemes are described to help to understand the present invention, and are not meant to restrict the scope of the present invention in any way.

Preparation of the Compound of Formula (2)

The compound of formula (2) is commercially available, or can be synthesized by using well known techniques in the art such as those described in EP 0 333 020 A2. The compound of formula (2) may be used in a next reaction in isolated form, or may be synthesized in situ before use. If the compound of formula (2) is used in a next reaction without isolation, it can be used as a solution. The solvent for dissolving the compound of formula (2) is preferably same as one used in the next reaction. Thus, as long as the dissolving solvent does not give adverse effects to the next reaction, it is not particularly limited. However, one or more selected from the group consisting of 1,2-dichloroethane, chloroform, toluene, N,N-dimethylformamide and N-methylpyrrolidinone may be preferably used as the dissolving solvent. 1,2-dichloroethane is the most preferable in terms of reactivity and yield.

Furthermore, in the compound of formula (2), the compound of formula (4), wherein X is F; Y and Z are each Cl; and Q is N, is highly irritating to skin, and thus it is very difficult to handle it in isolated form. Therefore, as shown in the Reaction Scheme 2 below, it is preferable to use in situ the compound of formula (4) obtained by chlorinating the compound of formula (5), in the next reaction.

Reaction Scheme 2

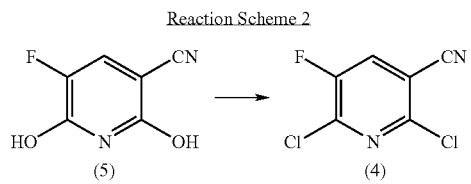

The above Reaction Scheme 2 is described in EP 0 333 020 A2. Particularly, an agent used for chlorinating the compound of formula (5) is phosphorus oxychloride, phosphorus pentachloride, or combinations thereof, preferably combinations of phosphorus oxychloride and phosphorus pentachloride. The amount of chlorination agent is not particularly limited, and may be selected within conventionally used ranges considering reaction conditions. For example, when the chlorination agent is a combination of phosphorus oxychloride and phosphorus pentachloride, phosphorus oxychloride and phosphorus pentachloride are used in 2~10 equiv and 1~10 equiv, respectively, preferably in 4~5 equiv and 3~5 equiv, to the compound of formula (5). The present reaction is carried out at a reflux temperature, preferably 50~150° C., more preferably 80~120° C.

Preparation of the Compound of Formula (1)

The following Reaction Scheme 3 shows the process for preparing the compound of formula (1) from the compound of formula (2):

Reaction Scheme 3

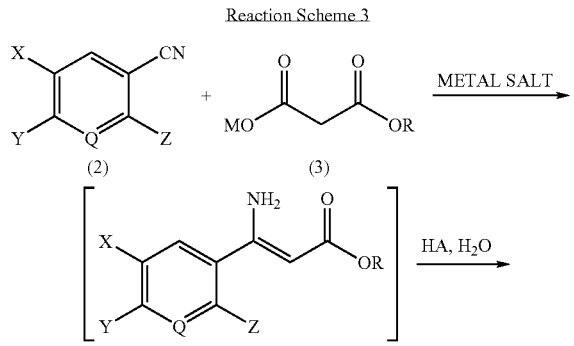

-continued

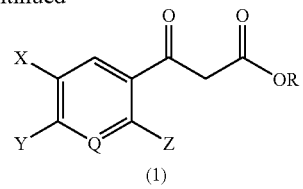

wherein Q, X, Y, Z, R and M are defined as above, HA represents inorganic acid or organic acid, and metal salt represents nickel salt, copper salt, indium salt or zinc salt.

In the Reaction Scheme 1, a significant amount of heat is generated at the step of adding alkyl alpha-bromoacetate, and thus to control it, alkyl alpha-bromoacetate was added slowly with monitoring the reaction heat. However, the reaction by the compounds of formula (2) and (3) in the Reaction Scheme 3 is a mild endothermic reaction. Thus, once the reactants are mixed, the reaction mixture should be heated for reflux in order to maintain the reaction. The resultant beta-aminoacrylate intermediate is hydrolyzed under the presence of aqueous acid solution to give beta-keto ester.

As organo nitrile compound, various aromatic nitrile compounds may be used in the range of defined substituents. Generally, the stronger electron-withdrawing group the compound has, the higher the reactivity of nitrile group is.

Q represents C—H, C—NO$_2$, C—F, C—OMe or N, preferably N or C—H, C—OMe, more preferably N. X represents halogen, preferably F. Preferably, Y and Z each independently represent F, Cl or Br, more preferably each independently F or Cl.

The compound of formula (3) is used in 1~2 equiv, preferably 1~1.5 equiv, to the compound of formula (2). R represents straight or branched C$_1$-C$_6$-alkyl or benzyl, preferably methyl, ethyl, isopropyl or t-butyl, and the most preferably ethyl.

M represents alkali metals, preferably lithium, sodium or potassium.

As metal salts, nickel salts, copper salts, indium salts, or zinc salts may be used. Preferably, the metal salt include, but are not limited to, its chloride, fluoride, bromide, iodide, acrylate, methacrylate, stearate and acetylacetonate. For example, nickel salts include nickel chloride, nickel bromide or nickel acetylacetonate. Copper salts include copper chloride, copper bromide, copper iodide or copper acetylacetonate. Indium salts include indium chloride, bromide, and iodide. Zinc salts include zinc chloride, zinc bromide, zinc iodide, zinc acrylate, zinc methacrylate, zinc stearate or zinc acetylacetonate. Among the metal salts, zinc salts are more preferable, and among zinc salts, zinc chloride is the most preferable. The amount of metal salts used in the reaction is varied depending on the reactivity of organonitrile compound. Generally, if the amount of metal salts is increased, the reaction rate is also increased, but the metal salt is preferably used in 0.01~1 time molar amount, more preferably 0.5~1 time molar amount, to the organonitrile compound of formula (2).

The reaction of the Scheme 2 may be carried out in any solvent as long as solvent used therein does not give detrimental effects to the reaction. As the reaction solvent, it is preferable to use one or more selected from the group consisting of 1,2-dichloroethane, chloroform, toluene, N,N-dimethylformamide and N-methylpyrrolidinone. 1,2-dichloroethane is the most preferable in view of reactivity and yield.

The reaction temperature may be selected in the range that the selected solvent can be refluxed, and the reaction system is continuously refluxed not to be cooled.

The intermediate of beta-aminoacrylate may be hydrolyzed in the presence of aqueous acid solution, as commonly known to a skilled person in the art. Aqueous acid solution may be used to the reaction system by adding acid and water separately, or adding acid and water in the form of aqueous solution. Acid used in the present invention includes, but are not limited to, inorganic acid or organic acid. Inorganic acid is preferable, and hydrochloric acid or sulfuric acid is more preferable. The aqueous acid solution is used in 1 or more equiv, preferably 10 or more equiv, and the most preferably 3~5 equiv to the compound of formula (2). The hydrolysis reaction is preferably carried out at a temperature of 20~100° C., more preferably 80~90° C.

Though the hydrolysis reaction may be carried out after the intermediate of beta-aminoacrylate is isolated, it is preferable to proceed the reaction as one-pot process by sequentially adding aqueous acid solution to the reaction system.

The present invention will be more specifically explained in the following examples. However, it should be understood that the following examples are intended to illustrate the present invention, and cannot limit the scope of the present invention in any manner.

EXAMPLE 1

Preparation of ethyl 3-(2,6-dichloro-5-fluoro-3-pyridyl)-3-oxopropanoate

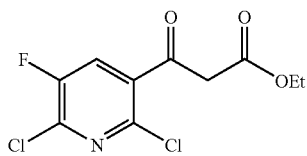

207 g of phosphorus oxychloride (POCl$_3$) was added to a reactor, which was cooled at 5° C. 20 g of 2,6-dihydroxy-5-fluoro-3-cyanopyridine and 205 g of phosphorus pentachloride (PCl$_5$) were then added thereto, and the mixture was stirred at reflux. After the reaction was completed, phosphorus oxychloride was removed therefrom through distillation under reduced pressure. The reactor was cooled to 5° C., and then 300 □ of 1,2-dichloroethane and 400 □ of water were added thereto. The organic layer was separated therefrom, and then 16 g of zinc chloride and 48 g of potassium ethylmalonate were added thereto, followed by reflux. After the reaction was completed, 78 □ of 6 N hydrochloric acid was added to the mixture at 90° C., which then was stirred at reflux at 90° C. for 4 hours. After confirming completion of the reaction by TLC, the solution was cooled to 20° C., and then an organic layer was separated therefrom. The organic layer was dried through distillation under reduced pressure, and 200 □ of a mixed solvent of ethanol and water (7:3, v/v ) was added thereto. Then, the reactor was cooled to 0~10° C., and was standing for 1 hour. Thus resulting solid was filtered and washed with 100 □ of a mixed solvent of ethanol and water (7:3, v/v ) having the same temperature, to obtain the title compound in the yield of 48% (35 g).

$^1$H NMR (400 MHz, CDCl$_3$) δ Enol Form(80%): 12.55 (s, 1 H), 7.82 (d, J=7.6 Hz, 1H), 5.81 (s, 1H), 4.27 (q, J=7.2 Hz, 2H), 1.33 (t, J=7.2 Hz, 3H). Keto Form (20%): 7.82 (d, J=7.6 Hz, 1H), 4.18 (q, J=7.2 Hz, 2H), 4.08 (s, 2H), 1.24 (t, J=7.2 Hz, 3H). Mass (APCI, m/z): 278 (M–H, 43), 264 (38), 232 (24), 214 (100).

EXAMPLE 2

Preparation of ethyl 3-(2,6-dichloro-5-fluoro-3-pyridyl)-3-oxopropanoate

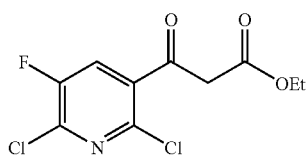

To 100 □ of 1,2-dichloroethane were added 10 g of 2,6-dichloro-5-fluoro-3-cyanopyridine, 3.6 g of zinc chloride, and 11 g of potassium ethylmalonate, and then the mixture was stirred at reflux. After the reaction was completed, 50 □ of 6 N hydrochloric acid was added to the mixture, which then was stirred at reflux at 90° C. for 4 hours. After confirming completion of the reaction by TLC, the solution was cooled to 20° C., and then an organic layer was separated therefrom. The organic layer was dried through distillation under reduced pressure, and 50 □ of a mixed solvent of ethanol and water ( 7:3, v/v ) was added thereto. Then, the reactor was cooled to 0~10° C., and was stirred for 1 hour. The resulting solid was filtered and washed with 25 □ of a mixed solvent of ethanol and water ( 7:3, v/v ) having the same temperature, to obtain the title compound in the yield of 80% (11.7 g)

$^1$H NMR (400 MHz, CDCl$_3$) δ Enol Form(80%): 12.55 (s, 1H), 7.82 (d, J=7.6 Hz, 1H), 5.81 (s, 1H), 4.27 (q, J=7.2 Hz, 2H), 1.33 (t, J=7.2 Hz, 3H). Keto Form (20%): 7.82 (d, J=7.6 Hz, 1H), 4.18 (q, J=7.2 Hz, 2H), 4.08 (s, 2H), 1.24 (t, J=7.2 Hz, 3H). Mass (APCI, m/z): 278 (M–H, 43), 264 (38), 232 (24), 214 (100).

EXAMPLE 3

Preparation of ethyl 2,4,5-trifluorobenzoylacetate

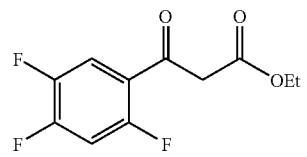

To 10 □ of 1,2-dichloroethane were added 1.0 g of 2,4,5-trifluorobenzonitrile, 0.43 g of zinc chloride, and 1.3 g of potassium ethylmalonate, and then the mixture was stirred at reflux. After the reaction was completed, 11 □ of 6 N hydrochloric acid was added to the mixture, which then was stirred at reflux at 90° C. for 1 hour. After confirming completion of the reaction by TLC, the solution was cooled to 20° C., and then an organic layer was separated therefrom. The organic layer was concentrated through distillation under reduced pressure. Thus resulted residue was purified by silica gel column chromatography (eluent: ethylacetate/n-hexane= 1/10, v/v) to obtain the title compound in the yield of 80% (1.2 g).

$^1$H NMR (400 MHz, CDCl$_3$) δ Enol Form(75%): 12.15 (s, 1H), 7.47 (dd, J=7.8 Hz, 1H), 7.04 (dd, J=7.8 Hz, 1H), 5.91 (s, 1H), 4.26 (q, J=7.2 Hz, 2H), 1.32 (t, J=7.2 Hz, 3H). Keto Form (25%): 7.66 (dd, J=7.8 Hz, 1H), 7.04 (dd, J=7.8 Hz, 1H), 4.16 (q, J=7.2 Hz, 2H), 4.10 (s, 2H), 1.21 (t, J=7.2 Hz, 3H). Mass (FAB, m/z): 247 (M+H).

EXAMPLE 4

Preparation of Ethyl Benzoylacetate

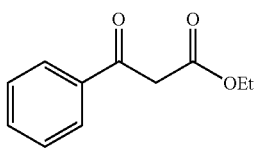

To 100 □ of 1,2-dichloroethane were added 5.5 □ of benzonitrile, 7.2 g of zinc chloride, and 11 g of potassium ethylmalonate, and then the mixture was stirred at reflux. After the reaction was completed, 100 □ of 6 N hydrochloric acid was added to the mixture, which then was stirred at reflux at 90° C. for 1 hour. After confirming completion of the reaction by TLC, the solution was cooled to 20° C., and then an organic layer was separated therefrom. The organic layer was concentrated through distillation under reduced pressure. Thus resulted residue was purified by silica gel column chromatography (eluent: ethylacetate/n-hexane=1/20, v/v) to obtain the title compound in the yield of 75% (7.6 g).

$^1$H NMR (400 MHz, CDCl$_3$) δ Enol Form (19%): 12.58 (s, 1H), 7.65~7.42 (m, 5H), 5.67 (s, 1H), 4.29 (q, J=7.2 Hz, 2H), 1.34 (t, J=7.2 Hz, 3H). Keto Form (81%): 7.95 (m, 2H), 7.59 (m, 1H), 7.48 (m, 2H), 4.21 (q, J=7.2 Hz, 2H), 3.99 (s, 2H), 1.25 (t, J=7.2 Hz, 3H). Mass (ESI, m/z): 193 (M+H).

EXAMPLE 5

Preparation of Ethyl Benzoylacetate

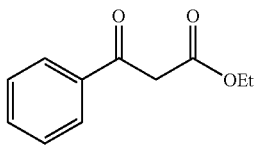

To 100 □ of 1,2-dichloroethane were added 5.5 □ of benzonitrile, 3.6 g of copper chloride and 11 g of potassium ethylmalonate, and then the mixture was stirred at reflux. After the reaction was completed, 100 □ of 6 N hydrochloric was added to the mixture, which then was stirred at reflux at 90° C. for 1 hour. After confirming completion of the reaction by TLC, the solution was cooled to 20° C., and then an organic layer was separated therefrom. The organic layer was concentrated through distillation under reduced pressure. Thus resulted residue was purified by silica gel column chromatography (eluent: ethylacetate/n-hexane=1/20, v/v) to obtain the title compound in the yield of 68% (7.0 g).

$^1$H NMR (400 MHz, CDCl$_3$) δ Enol Form(19%): 12.58 (s, 1H), 7.65~7.42 (m, 5H), 5.67 (s, 1H), 4.29 (q, J=7.2 Hz, 2H), 1.34 (t, J=7.2 Hz, 3H). Keto Form (81%): 7.95 (m, 2H), 7.59 (m, 1H), 7.48 (m, 2H), 4.21 (q, J=7.2 Hz, 2H), 3.99 (s, 2H), 1.25 (t, J=7.2 Hz, 3H). Mass (ESI, m/z): 193 (M+H).

INDUSTRIAL APPLICABILITY

The present invention has the following outstanding effects: (1) it is easy to control the reaction heat since the reaction is endothermic; (2) the preparation process is easy to handle by using non-lachrymatory alkali metal salt of mono-alkyl malonate, and (3) the present method has high reproducibility by using metal salt which the stirring is easier than zinc metal of high density, as catalyst.

The invention claimed is:

1. A process for preparing a beta-keto ester compound of formula (1):

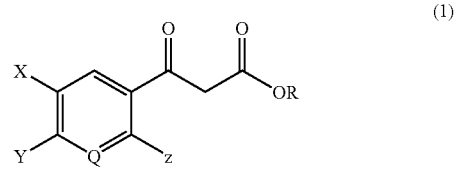

wherein,

Q represents C—H, C—NO$_2$, C—F, C—OMe or N,

X, Y and Z each independently represent H, halogen or NO$_2$,

R represents straight or branched C$_1$-C$_6$-alkyl or benzyl, and

M represents alkali metal, comprising the steps of, 1) obtaining a compound of formula (6) by reacting a compound of formula (2) with a compound of formula (3) in the presence of metal salt;

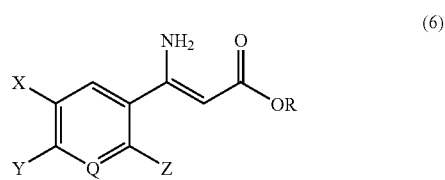

wherein Q, X, Y, Z and R are defined as above,

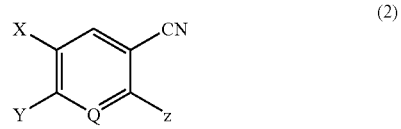

wherein Q, X, Y, and Z are defined as above, and

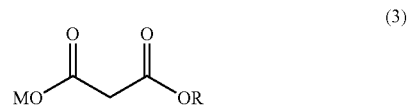

wherein R is defined as above and M represents alkali metal, and 2) hydrolyzing the compound obtained from step 1) in the presence of aqueous acid solution.

2. The process according to claim 1, wherein the reaction is carried out by one-pot reaction.

3. The process according to claim 1, wherein the reaction is carried out in one or more solvents selected from the group consisting of 1,2-dichloroethane, chloroform, toluene, N,N-dimethylformamide and N-methylpyrrolidinone.

4. The process according to claim 1, wherein R is methyl, ethyl, isopropyl or t-butyl.

5. The process according to claim 1, wherein M is lithium, sodium or potassium.

6. The process according to claim 1, wherein the compound of formula (3) is used in 1~2 equiv to the compound of formula (2).

7. The process according to claim 6, wherein the compound of formula (3) is used in 1~1.5 equiv to the compound of formula (2).

8. The process according to claim 1, wherein the metal salt is nickel salt, copper salt, indium salt or zinc salt.

9. The process according to claim 1 or 8, wherein the metal salt is selected from the group consisting of nickel chloride, nickel bromide, nickel acetylacetonate, copper chloride, copper bromide, copper iodide, copper acetylacetonate, indium chloride, indium bromide, indium iodide, zinc chloride, zinc bromide, zinc iodide, zinc acrylate, zinc methacrylate, zinc stearate and zinc acetylacetonate.

10. The process according to claim 1 or 8, wherein the metal salt is used in 0.01~1 equiv to the compound of formula (2).

11. The process according to claim 10, wherein the metal salt is used in 0.5~1 equiv to the compound of formula (2).

12. The process according to claim 1, wherein the aqueous acid solution is an aqueous inorganic acid solution.

13. The process according to claim 12, wherein the inorganic acid is hydrochloric acid or sulfuric acid.

14. The process according to claim 1, wherein the hydrolyzing reaction is carried out at the temperature range of 20 to 100° C.

15. The process according to claim 14, wherein the hydrolysis reaction is carried out at the temperature range of 80 to 90° C.

16. The process according to claim 1, wherein the compound of formula (2) is prepared by chlorinating the hydroxyl group of a compound of formula (5):

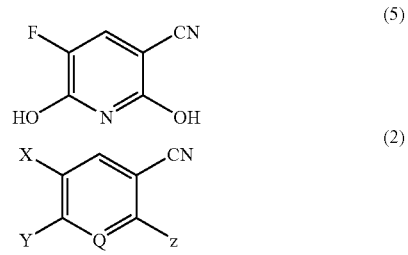

wherein Q represents N; X represents F; Y and Z each represent Cl.

17. The process according to claim 16, wherein the chlorination is carried out in the presence of 2~10 equiv of phosphorus oxychloride, and 1~10 equiv of phosphorus pentachloride, to the compound of formula (5).

* * * * *